(12) United States Patent
Kawamura et al.

(10) Patent No.: US 7,794,739 B2
(45) Date of Patent: *Sep. 14, 2010

(54) NUCLEIC ACID BASED COMPOSITION FOR CELL PROLIFERATION

(75) Inventors: Mitsuaki Kawamura, Kyoto (JP); Shigeo Shinohara, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 814 days.

This patent is subject to a terminal disclaimer.

(21) Appl. No.: 10/510,738

(22) PCT Filed: Apr. 3, 2003

(86) PCT No.: PCT/JP03/04247

§ 371 (c)(1), (2), (4) Date: Oct. 12, 2004

(87) PCT Pub. No.: WO03/084485

PCT Pub. Date: Oct. 16, 2003

(65) Prior Publication Data

US 2005/0222076 A1    Oct. 6, 2005

(30) Foreign Application Priority Data

Apr. 9, 2002    (JP) ............... 2002-106300

(51) Int. Cl.
*A61K 8/00*    (2006.01)
*A61K 8/02*    (2006.01)
*A61K 31/70*    (2006.01)

(52) U.S. Cl. ......................... 424/401; 514/47
(58) Field of Classification Search ............. 424/401; 514/47

See application file for complete search history.

(56) References Cited

U.S. PATENT DOCUMENTS

| | | | | |
|---|---|---|---|---|
| 4,544,559 A | * | 10/1985 | Gil et al. | 426/72 |
| 4,758,533 A | * | 7/1988 | Magee et al. | 438/662 |
| 5,053,230 A | * | 10/1991 | Gazzani | 424/582 |
| 5,066,500 A | | 11/1991 | Gil et al. | |
| 5,182,269 A | * | 1/1993 | Gazzani | 514/44 |
| 5,602,109 A | * | 2/1997 | Masor et al. | 514/45 |
| 6,203,805 B1 | * | 3/2001 | Collins et al. | 424/401 |
| 2002/0141955 A1 | * | 10/2002 | Zimmerman et al. | 424/62 |
| 2003/0068349 A1 | | 4/2003 | Jentzsch et al. | |
| 2004/0116373 A1 | | 6/2004 | Okuda et al. | |

FOREIGN PATENT DOCUMENTS

| | | |
|---|---|---|
| EP | 0256472 | 2/1988 |
| EP | 0 360 882 A1 | 4/1990 |
| JP | 63-183535 | 7/1988 |
| JP | 6-48934 | 2/1994 |
| JP | 9-295915 | 11/1997 |
| JP | 2001-31549 | 2/2001 |
| JP | 2003-40729 | 2/2003 |
| JP | 2001-278783 | 10/2003 |
| JP | 2001-316240 | 11/2003 |
| WO | WO 98/32429 | 7/1998 |

OTHER PUBLICATIONS

Stefano Thellung et al., "Polydeoxyribonucleotides Enhance the Proliferation of Human Skin Fibroblasts: Involvement of $A_2$ Purinergic Receptor Subtypes," Life Science, vol. 64. No. 18, 1999, pp. 1661-1674.

Croucher, L.J. et al., 'Extracellular ATP and UTP stimulate cartilage proteoglycan and collagen accumulation in bovine articular chondrocyte pellet cultures,' Biochimica et Biophysica Acta 1502:297-306 (2000).

International Search Report of International Application PCT/JP2004/01528, filed Oct. 8, 2004.

Office Action mailed Jan. 9, 2008, in U.S. Appl. No. 10/574,696.

Reply to Office Action filed Jul. 9, 2008, in U.S. Appl. No. 10/574,696.

Translation of International Preliminary Report on Patentability of International Application PCT/JP2004/01528, filed Oct. 8, 2004.

* cited by examiner

Primary Examiner—Yong S Chong
Assistant Examiner—Jody L Karol
(74) Attorney, Agent, or Firm—Finnegan, Henderson, Farabow, Garrett & Dunner, L.L.P.

(57) ABSTRACT

A method for effectively exerting a cell proliferation promoting effect of a purine nucleic acid-related substance, and a composition for cell proliferation containing a purine nucleic acid-related substance and a pyrimidine nucleic acid-related substance. Also a method for potentiating the cell proliferation promoting effect of the purine nucleic acid-related substance by using the purine nucleic acid-related substance in combination with the pyrimidine nucleic acid-related substance and a method for promoting cell proliferation, where the method includes the step of applying the purine nucleic acid-related substance in combination with the pyrimidine nucleic acid-related substance to the skin or mucosa.

6 Claims, 1 Drawing Sheet

NUCLEIC ACID BASED COMPOSITION FOR CELL PROLIFERATION

TECHNICAL FIELD

The present invention relates to a composition for cell proliferation that effectively exerts a cell proliferation effect of a purine nucleic acid-related substance. Further, the present invention relates to a method for potentiating the cell proliferation effect of the purine nucleic acid-related substance. The present invention also relates to a method for promoting cell proliferation by effectively exerting the cell proliferation effect of the purine nucleic acid-related substance.

BACKGROUND OF THE INVENTION

It is known that purine nucleic acid-related substances, such as adenosine, adenosine phosphate, and salts thereof, exhibit a moisturizing effect when applied to the skin by increasing the number of free amino acids in the horny cell layer, and, in addition, function to stimulate turnover thereby preventing drying and aging of the skin and improving the condition of rough skin. In order to obtain this effect, the application of purine nucleic acid-related substances to external preparations, such as a cosmetic, pharmaceutical or quasi-pharmaceutical preparations has been examined. It is known that purine nucleic acid-related substances have a cell proliferation promoting effect (Life Sciences, Vol. 64, No. 18, pp. 1661-1674, 1999), and it is assumed that the cell-proliferation promoting effect relates to the above-described various effects.

However, since these purine nucleic acid-related substances have high hydrophilicity, percutaneous absorption is difficult to carry out.

In order to overcome such drawbacks, for a long time a method has been sought that can more effectively exert the cell-proliferation promoting effect of purine nucleic acid-related substances when applied to the skin, etc.

SUMMARY OF THE INVENTION

An object of the present invention is to provide a method for effectively exerting the cell proliferation promoting effect of a purine nucleic acid-related substance. More specifically, an object of the present invention is to provide a composition that potentiates the cell-proliferation promoting effect of the purine nucleic acid-related substance, to thereby effectively proliferate cells. Another object of the present invention is to provide a method for potentiating the cell proliferation promoting effect of the purine nucleic acid-related substance. Still another object of the present invention is to provide a method for effectively exerting the cell proliferation effect of the purine nucleic acid-related substance, to thereby promote cell proliferation.

The present inventors carried out intensive research to develop a method for potentiating the cell proliferation promoting effect of the purine nucleic acid-related substance and found that the above-described objects can be accomplished by the combined use of a pyrimidine nucleic acid-related substance with the purine nucleic acid-related substance. The present invention has been developed on the basis of the above findings.

More specifically, the present invention relates to the following compositions for cell proliferation:

Item 1. A composition for cell proliferation containing a purine nucleic acid-related substance and a pyrimidine nucleic acid-related substance.

Item 2. A composition for cell proliferation according to Item 1, wherein the purine nucleic acid-related substance is at least one member selected from adenine nucleic acid-related substances and the pyrimidine nucleic acid-related substance is at least one member selected from uracil nucleic acid-related substances.

Item 3. A composition for cell proliferation according to Item 1 or 2, wherein the purine nucleic acid-related substance is adenosine monophosphate or a salt thereof and the pyrimidine nucleic acid-related substance is uridine monophosphate or a salt thereof.

Item 4. A composition for cell proliferation according to any one of Items 1 to 3, wherein the composition contains the purine nucleic acid-related substance in a proportion of at least 0.01% by weight.

Item 5. A composition for cell proliferation according to any one of Items 1 to 3, wherein the composition contains the purine nucleic acid-related substance in a proportion of 0.01 to 10% by weight.

Item 6. A composition for cell proliferation according to any one of Items 1 to 5, wherein the composition contains the pyrimidine nucleic acid-related substance in a ratio of 0.01 to 100 parts by weight per part by weight of the purine nucleic acid-related substance contained in the composition.

Item 7. A composition for cell proliferation according to any one of Items 1 to 6 used for an externally-applied composition for the skin or mucosa.

Item 8. A composition for cell proliferation according to any one of Items 1 to 7 used for a cosmetic or an externally-applied medical or quasi-medical drug.

Item 9. A composition for cell proliferation according to any one of Items 1 to 8 that is used for a purpose selected from the group consisting of anti-aging, moisturizing, anti-acne, skin whitening, anti-sagging, anti-dullness, anti-wrinkle, hair growth, anti-dandruff, nail beautifying, and wound healing.

Item 10. A composition for cell proliferation according to any one of Items 1 to 8 that is used for a purpose selected from the group consisting of anti-aging, moisturizing, anti-acne, skin whitening, anti-sagging, anti-dullness, anti-wrinkle, hair growth, nail beautifying, and wound healing.

Item 11. A composition for cell proliferation according to any one of Items 1 to 8 that is used for the purpose of an anti-wrinkle.

The present invention also relates to the following methods for potentiating the cell proliferation promoting effect:

Item 12. A method for potentiating a cell proliferation promoting effect of a purine nucleic acid-related substance by using a purine nucleic acid-related substance in combination with a pyrimidine nucleic acid-related substance.

Item 13. A method for potentiating a cell proliferation promoting effect according to Item 12, wherein the purine nucleic acid-related substance is at least one member selected from adenine nucleic acid-related substances and the pyrimidine nucleic acid-related substance is at least one member selected from uracil nucleic acid-related substances.

Item 14. A method for potentiating a cell proliferation promoting effect according to Item 12 or 13, wherein the purine nucleic acid-related substance is at least one member selected from the group consisting of adenine, adenosine, adenosine phosphates, hypoxanthine, inosine, inosinic acid, and salts thereof, and the pyrimidine nucleic acid-related substance is at least one member selected from the group consisting of uracil, uridine, uridine phosphates, deoxyuridine, deoxyuridine phosphates, and salts thereof.

Item 15. A method for potentiating a cell proliferation promoting effect according to any one of Items 12 to 14, wherein the purine nucleic acid-related substance is adenosine monophosphate or a salt thereof, and the pyrimidine nucleic acid-related substance is uridine monophosphate or a salt thereof.

Item 16. A method for potentiating a cell proliferation promoting effect according to any one of Items 12 to 15, wherein the method comprises using the pyrimidine nucleic acid-related substance in a ratio of 0.01 to 100 parts by weight per part by weight of the purine nucleic acid-related substance.

Item 17. A method for potentiating a cell proliferation promoting effect according to any one of Items 12 to 16, wherein the method comprises incorporating the pyrimidine nucleic acid-related substance into a composition containing the purine nucleic acid-related substance.

Item 18. A method for potentiating a cell proliferation promoting effect according to Item 17, wherein the composition contains the purine nucleic acid-related substance in a proportion of at least 0.01% by weight.

Item 19. A method for potentiating a cell proliferation promoting effect according to Item 17 or 18, wherein the composition contains the purine nucleic acid-related substance in a proportion of 0.01 to 10% by weight.

Item 20. A method for potentiating a cell proliferation promoting effect according to any one of Items 17 to 19, wherein the composition is an externally-applied composition for the skin or mucosa.

Item 21. A method for potentiating a cell proliferation promoting effect according to any one of Items 17 to 20, wherein the composition is a cosmetic or an externally-applied medical or quasi-medical drug.

Item 22. A method for potentiating a cell proliferation promoting effect according to any one of Items 17 to 21, wherein the composition is used for a purpose selected from the group consisting of anti-aging, moisturizing, anti-acne, skin whitening, anti-sagging, anti-dullness, anti-wrinkle, hair growth, anti-dandruff, nail beautifying, and wound healing.

Item 23. A method for potentiating a cell proliferation promoting effect according to any one of Items 17 to 21, wherein the composition is used for a purpose selected from the group consisting of anti-aging, moisturizing, anti-acne, skin whitening, anti-sagging, anti-dullness, anti-wrinkle, hair growth, nail beautifying, and wound healing.

Item 24. A method for potentiating a cell proliferation promoting effect according to any one of Items 17 to 21, wherein the composition is used for the purpose of an anti-wrinkle.

The present invention further relates to the following methods for promoting cell proliferation:

Item 25. A method for promoting cell proliferation by applying to the skin or mucosa a purine nucleic acid-related substance in combination with a pyrimidine nucleic acid-related substance.

Item 26. A method for promoting cell proliferation according to Item 25, wherein the purine nucleic acid-related substance is at least one member selected from adenine nucleic acid-related substances and the pyrimidine nucleic acid-related substance is at least one member selected from uracil nucleic acid-related substances.

Item 27. A method for promoting cell proliferation according to Item 25 or 26, wherein the purine nucleic acid-related substance is at least one member selected from the group consisting of adenine, adenosine, adenosine phosphates, hypoxanthine, inosine, inosinic acid, and salts thereof, and the pyrimidine nucleic acid-related substance is at least one member selected from the group consisting of uracil, uridine, uridine phosphates, deoxyuridine, deoxyuridine phosphates, and salts thereof.

Item 28. A method for promoting cell proliferation according to any one of Items 25 to 27, wherein the purine nucleic acid-related substance is adenosine monophosphate or a salt thereof, and the pyrimidine nucleic acid-related substance is uridine monophosphate or a salt thereof.

Item 29. A method for promoting cell proliferation according to any one of Items 25 to 28, wherein the method comprises using the pyrimidine nucleic acid-related substance in a ratio of 0.01 to 100 parts by per part by weight of the purine nucleic acid-related substance.

Item 30. A method for promoting cell proliferation according to anyone of Items 25 to 29, wherein the method comprises applying to the skin or mucosa a composition containing the purine nucleic acid-related substance and the pyrimidine nucleic acid-related substance.

Item 31. A method for promoting cell proliferation according to Item 30, wherein the composition contains the purine nucleic acid-related substance in a proportion of at least 0.01% by weight.

Item 32. A method for promoting cell proliferation according to Item 31, wherein the composition contains the purine nucleic acid-related substance in a proportion of 0.01 to 10% by weight.

Item 33. A method for promoting cell proliferation according to any one of Items 30 to 32, wherein the composition is an externally-applied composition for the skin or mucosa.

Item 34. A method for promoting cell proliferation according to any one of Items 30 to 33, wherein the composition is a cosmetic or an externally-applied medical or quasi-medical drug.

Item 35. A method for promoting cell proliferation according to any one of Items 25 to 34, wherein the composition is used for a purpose selected from the group consisting of anti-aging, moisturizing, anti-acne, skin whitening, anti-sagging, anti-dullness, anti-wrinkle, hair growth, anti-dandruff, nail beautifying, and wound healing.

Item 36. A method for promoting cell proliferation according to any one of Items 25 to 34, wherein the composition is used for a purpose selected from the group consisting of anti-aging, moisturizing, anti-acne, skin whitening, anti-sagging, anti-dullness, anti-wrinkle, hair growth, nail beautifying, and wound healing.

Item 37. A method for promoting cell proliferation according to any one of Items 25 to 34, wherein a composition is used for the purpose of an anti-wrinkle.

The invention is further used in the following modes of embodiments:

Item 38. Use of a purine nucleic acid-related substance and a pyrimidine nucleic acid-related substance for the preparation of a composition for cell proliferation.

Item 39. Use of a pyrimidine nucleic acid-related substance for potentiating a cell proliferation promoting effect of a purine nucleic acid-related substance.

Item 40. Use of a purine nucleic acid-related substance and a pyrimidine nucleic acid-related substance for promoting cell proliferation.

Item 41. Use of a purine nucleic acid-related substance and a pyrimidine nucleic acid-related substance for an anti-wrinkle effect.

Figure 1:
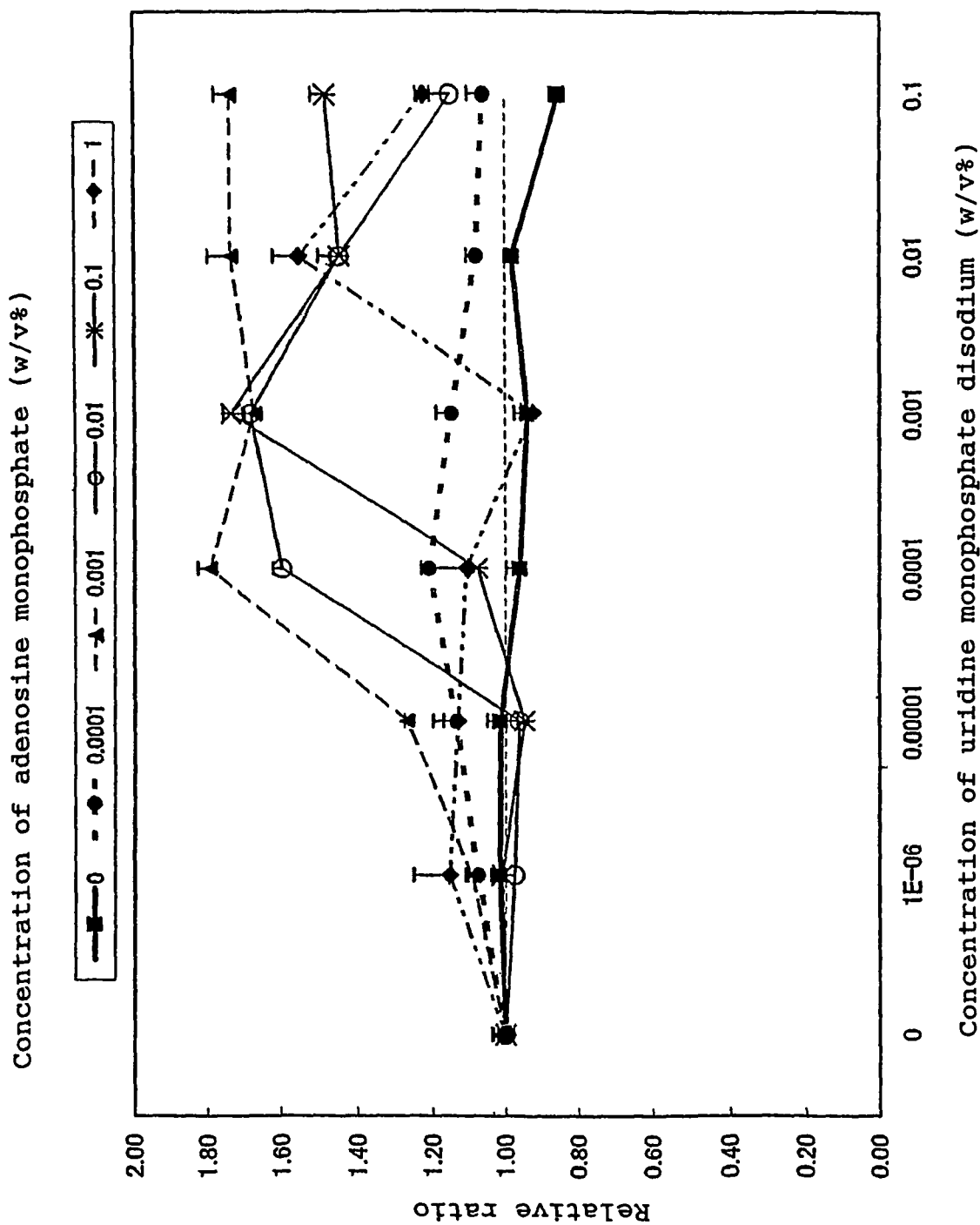
FIG. 1 shows that, in Experimental Example 1, the cell proliferation promoting effect of adenosine monophosphate disodium in human keratinocyte is potentiated when used in combination with uridine monophosphate disodium. The abscissa represents the concentration (W/V %) of uridine monophosphate disodium used in conjunction with adenosine monophosphate disodium. The ordinate represents the relative ratio (ratio of cont.) of the number of cells of each test sample relative to the number of cells of a comparative test sample set as 1. The comparative test sample was prepared without adding uridine monophosphate disodium to a solution containing adenosine monophosphate disodium.

BEST MODE FOR CARRYING OUT THE INVENTION (1) Composition for Cell Proliferation A composition for cell proliferation of the present invention contains a pyrimidine nucleic acid-related substance in addition to a purine nucleic acid-related substance.

Purine nucleic acid-related substances usable in the invention are those that exhibit physiological functions when applied to the skin or mucosa. Examples include a wide variety of purine nucleic acid-related substances that can be incorporated into cosmetics, externally-applied medical and quasi-medical drugs. Those that are water soluble or hydrophilic are preferable. Examples of purine nucleic acid-related substances include adenine nucleic acid-related substances such as adenine, adenosine, adenosine phosphate (for example, adenosine 2'-monophosphate, adenosine 3'-monophosphate, adenosine 5'-monophosphate, adenosine 5'-diphosphate, adenosine 5'-triphosphate, cyclic adenosine monophosphate, adenylosuccinic acid, nicotinamide adenine monodinucleotide (NMN), nicotinamide adenine dinucleotide (NAD), nicotinamide adenine dinucleotide phosphate (NADP), flavin adenine dinucleotide (FAD), etc.), metabolites of adenine, adenosine, or adenosine phosphates (for example, hypoxanthine, inosine, inosinic acid, etc.), and salts thereof; and guanine nucleic acid-related substances such as guanine, guanosine, guanosine monophosphate (for example, guanosine 3'-monophosphate, guanosine 5'-monophosphate, guanosine 5'-diphosphate and guanosine 5'-triphosphate, etc.), metabolites of guanine, guanosine, or guanosine phosphate (for example, xanthylic acid, xanthin, etc.), and salts thereof.

Among them, the above-mentioned adenine nucleic acid-related substances can be suitably used as the purine nucleic acid-related substance in the invention. Preferable among these are adenosine monophosphates, metabolites thereof, and their salts, and particularly preferable are adenosine monophosphates, and salts thereof. Adenosine monophosphate is preferable as the adenosine phosphate usable in the invention, and adenosine 5'-monophosphate (AMP) is particularly preferable.

Examples of salts include alkali metal salts, such as sodium salts, potassium salts, etc.; alkaline earth metal salts, such as calcium salts, magnesium salts, barium salts, etc.; basic amino acid salts, such as arginine, lysine, etc.; ammonium salts, such as ammonium salts, tricyclohexylammonium salts, etc.; various kinds of alkanolamine salts, such as mono-ethanolamine salts, diethanolamine salts, triethanolamine salts, monoisopropanolamine salts, diisopropanolamine salts, and triisopropanolamine salts, etc. Preferable among these are alkali metal salts, such as sodium salts, etc. Specific examples of alkali metal salts include adenosine monophosphate monosodium and adenosine monophosphate disodium.

Such purine nucleic acid-related substances may be used alone or in combination of two or more species in the composition for cell proliferation of the present invention.

The purine nucleic acid-related substances can be incorporated into the composition for cell proliferation in a proportion of at least 0.01% by weight. Preferable is at least 1% by weight and more preferable is at least 3% by weight. In view of the effects of the present invention, there is no general limitation to the upper limit of the proportion for incorporating the purine nucleic acid-related substance into the composition for cell proliferation. The proportion varies depending on the purpose of the composition for cell proliferation, and is usually suitably selected from the range of 0.01 to 10% by weight, preferably 1 to 10% by weight, and more preferably 3 to 6% by weight, and adjusted considering other factors in combination with other components, feeling of use, etc.

The pyrimidine nucleic acid-related substances usable in the invention are not limited and examples include a wide variety of pyrimidine nucleic acid-related substances that can be incorporated into cosmetics, externally-applied medical and quasi-medical drugs as with the purine nucleic acid-related substances. Those that are water soluble or hydrophilic are preferable. Specific examples of pyrimidine nucleic acid-related substances include uracil nucleic acid-related substances, such as uracil, uridine, uridine phosphates [uridine monophosphates (uridine 5'-monophosphate, uridine 3'-monophosphate and uridine 2'-monophosphate), uridine diphosphate, uridine triphosphate, cyclic uridine monophosphate, etc.], deoxyuridine, deoxyuridine phosphates [5'-deoxyuridine diphosphate (dUDP), 5'-deoxyuridine monophosphate (dUMP), etc.], and salts thereof; cytosine nucleic acid-related substances, such as cytosine, cytidine, cytidine phosphates [cytidine monophosophate (CMP) (cytidine 5'-monophosphate, cytidine3'-monophosphate, cytidine 2'-monophosphate), cytidine triphosphate (CTP), cytidinediphosphate (CDP)], deoxycytidine, deoxycytidine phosphates (5'-deoxycytidine triphosphate (dCTP), 5'-deoxycytidine diphosphate (dCDP), 5'-deoxycytidine monophosphate (dCMP), and salts thereof; thymine nucleic thereof; thymine nucleic acid related-substances, such as thymine, thymidine, thymidine phosphates [thymidine monophosphate (dTMP), thymidine diphosphate (dTDP), thymidine triphosphate (dTTP), etc.], orotic acid, orotidine 5'-phosphate, and salts thereof.

Any pyrimidine nucleic acid-related substances are usable irrespective of the purity insofar as each of the above-mentioned components are contained. Usable as the pyrimidine nucleic acid-related substances are plant extracts containing the above-mentioned components, such as Brassicaceae plant extracts (especially, seed extract), a Leguminosae plant extracts, etc.

The above-mentioned uracil nucleic acid-related substances are preferably used as the pyrimidine nucleic acid-related substances. Preferable are uridine, uridine phosphate, and salts thereof, and particularly preferable are uridine phosphates, and salts thereof. It is particularly preferable to use uridine monophosphate, especially uridine 5'-monophosphate (UMP), as the uridine phosphate.

Examples of the salts mentioned in the above include sodium salts, potassium salts, and like alkali metal salts; calcium salts, magnesium salts, barium salts, and like alkaline earth metal salts; arginine, lysine, and like basic amino acid salts; ammonium salts, tricyclohexylammonium salts and like ammonium salts; a wide variety of alkanolamine salts, such as monoethanolamine salt, diethanolamine salts, triethanolamine salts, monoisopropanolamine salts, diisopropanolamine salts, triisopropanolamine salts, etc.

Preferable among these are alkali metal salts such as sodium salts. Specific examples of alkali metal salts include uridine monophosphate monosodium and uridine monophosphate disodium.

Such pyrimidine nucleic acid-related substances may be used alone or in combination of two or more species in the composition for cell proliferation of the present invention.

The proportion for incorporating the pyrimidine nucleic acid-related substances into the composition for cell proliferation of the present invention is not limited insofar as the above-described effects can be obtained, and can be suitably selected from a range such that the pyrimidine nucleic acid-related substance is in a ratio of 0.01 to 100 parts by weight, preferably 0.01 to 10 parts by weight, and more preferably 0.01 to 1 part by weight per part by weight of the purine nucleic acid-related substance contained in the composition.

The proportion of the pyrimidine nucleic acid-related substance in the composition for cell proliferation can be suitably selected from the range of 0.0001 to 50% by weight, preferably 0.0001 to 10% by weight, and more preferably 0.0001 to 1% by weight, considering the proportion of the purine nucleic acid-related substance.

The combined use of the above-described purine nucleic acid-related substances and pyrimidine nucleic acid-related substances gives the composition of the present invention the effect of promoting proliferation of cells, such as skin cells, cells of skin appendages (hair, sebaceous glands, nails, etc.), or mucosa cells, etc. Therefore, the composition of the present invention can be widely used for a cosmetic or an externally-applied medical or quasi-medical drug as a composition for the proliferation of cells or composition for promoting cell proliferation. More specifically, the composition of the invention can be used as a cosmetic or an externally-applied medical or quasi-medical drug for the purpose of anti-aging, moisturizing, anti-acne, skin whitening, anti-wrinkle, anti-sagging, anti-dullness, hair growth, anti-dandruff, nail beautifying, and wound healing. Preferable among these are a wide variety of externally-applied medical agents for the purpose of anti-aging, moisturizing, anti-acne, skin whitening, anti-wrinkle, anti-sagging, anti-dullness, hair growth, nail beautifying, and wound healing. In particular, the composition of the present invention can effectively demonstrate an anti-wrinkle effect, and thus is useful as an externally-applied medical agent for the purpose of anti-wrinkle.

The composition of the present invention is preferably used as externally-applied agent for the skin. Externally-applied agents for the skin include a wide variety of hair care products such as hair restorers and hair growth agents, in addition thereto, shampoos, rinses, and hair lotions (including a tonic and a liquid) that have a hair restoration or hair growth effect.

The composition of the invention can take any form without limitation insofar as it is applicable to the skin or mucosa, such as an aqueous solution, a solubilized form, an emulsified form, a dispersed powder, a water/oil two layer-type, etc. Specific examples include solutions, oil solutions, lotions, liniments, emulsions, suspensions, creams, ointments, etc. Examples of cosmetics include lotions; emollient emulsions, milky lotions, nourishing emulsions, cleansing emulsions, and like emulsions; emollient creams, massage creams, cleansing creams, makeup creams, and like creams; etc. Examples of hair care products include hair tonics, hair creams, hair lotions, aerosols (air sprays), mousses, shampoos, rinses, liquids, etc.

The composition for cell proliferation of the present invention, insofar as the effects of the invention are not impaired, may contain, as required, a wide range of well-known components used in externally-applied compositions suitable for the skin or mucosa like cosmetics and externally-applied medical/quasi-medical drugs. Examples of such components include humectants, UV absorbers, UV dispersants, vitamins, plant extracts, astringents, anti-inflammatory agents (antiphlogistic agents), whiteners, cell activators, vasodilators, blood circulation accelerators, skin function accelerators, and the like in addition to surfactants, coloring matter (dyes, pigments), aromatics, antiseptics, bactericides (antibacterials), thickeners, antioxidants, sequestering agents, refrigerants, deodorizers, and the like. Well-known bases or carriers can also be used according to the above-mentioned various forms.

Examples of the above-mentioned components include anionic surfactants, such as salts of higher fatty acids, alkylsulfonate salts, polyoxyethylene alkyl ether sulfates, alkyl ether phosphates, N-acylamino acid salts, acyl N-methyl taurine salts, etc.; cationic surfactants, such as alkyl trimethylammonium chlorides, dialkyldimethylammonium chlorides, etc.; amphoteric surfactants, such as alkyldimethylaminoacetate betaines, alkylamidedimethylaminoacetate betaines, 2-alkyl-N-carboxy-N-hydroxyimidazolinium betaines, etc.; nonionic surfactants, such as polyoxyethylene-bases, polyhydric alcohol ester-bases, ethylene oxide/propylene oxide block copolymers, etc. Any high molecular weight surfactants or natural surfactants can also be used without limitation.

Examples of antiseptics include ethyl p-hydroxybenzoate, salicylic acid, sorbic acid, etc. Examples of thickeners include xanthane gum, carboxymethyl cellulose sodium, carboxy vinyl polymers, etc. Examples of sequestering agents include sodium salts of ethylenediamine tetra-acetic acid, phosphoric acid, citric acid, etc.

The composition for cell proliferation of the present invention can be directly applied to or sprayed onto the skin or mucosa as a cosmetic or an externally-applied medical or quasi-medical drug. The composition can be applied to the skin or mucosa once to 5 or 6 times per day according to the age of the user (human), the gender, the intended use, the condition of the affected part of the skin, etc. A single dose amount of the composition for cell proliferation of the invention is not limited, and, for example, can be suitably adjusted such that the amount of the composition applied to the skin or mucosa is within the range of 0.5 to 10 mg/cm$^2$.

As described above, the combined use of a pyrimidine nucleic acid-related substance with a purine nucleic acid-related substance can potentiate the cell proliferation promoting effect of a purine nucleic acid-related substance. Accordingly, the present invention provides the use of a purine nucleic acid-related substance and a pyrimidine nucleic acid-related substance for the preparation of a composition for cell proliferation.

(2) A Method for Potentiating the Cell Proliferation Promoting Effect of a Purine Nucleic Acid-Related Substance The present invention provides a method for potentiating the cell proliferation promoting effect of a purine nucleic acid-related substance. The method can be carried out by using the purine nucleic acid-related substance in combination with a pyrimidine nucleic acid-related substance.

The purine nucleic acid-related substance and the pyrimidine nucleic acid-related substance usable in the invention include the previously-described substances. A preferable example of the purine nucleic acid-related substance is an adenine nucleic acid-related substance. Particularly preferable among the adenine nucleic acid-related substances are adenosine phosphates, metabolites thereof, and their salts, and particularly preferable are adenosine phosphates and a salt thereof. Specific examples of adenosine phosphates include adenosine monophosphates, in particular adenosine 5'-monophosphate (AMP). Preferable examples of pyrimidine nucleic acid-related substance include an uracil nucleic acid-related substance. Preferable among the uracil nucleic acid-related substances are uridine, uridine phosphates, and salts thereof, and particularly preferable are uridine phosphates and salts thereof. Specific examples of the uridine phosphates include uridine monophosphates, in particular uridine 5'-monophosphate (UMP).

The ratio for blending the pyrimidine nucleic acid-related substance relative to the purine nucleic acid-related substance is 0.01 to 100 parts by weight per part by weight of the purine nucleic acid-related substance, preferably 0.01 to 10 parts by weight, and more preferably 0.01 to 1 part by weight.

The method of the present invention is used for preparing a composition for use in the application of a purine nucleic acid-related substance to the skin or mucosa. More specifically, the method of the present invention is used for preparing a composition that exhibits the effects of anti-aging, moisturizing, anti-acne, skin whitening, anti-wrinkle, anti-sagging, anti-dullness, hair growth, anti-dandruff, nail beautifying, wound healing, etc. due to the cell proliferation promoting effect of a purine nucleic acid related substance. Preferably among the compositions that are prepared according to the method of the present invention and exhibit the above-described effects are those that exhibit the effects of anti-aging, moisturizing, anti-acne, skin whitening, anti-wrinkle, anti-sagging, anti-dullness, hair growth, nail beautifying, wound healing, etc. Particularly preferable is a composition that exhibits an anti-wrinkle effect. According to the invention, the combined use of a pyrimidine nucleic acid-related substance with a purine nucleic acid-related substance potentiates the cell proliferation promoting effect of the purine nucleic acid-related substance, and thus a composition with an excellent effect as described above can be prepared.

To prepare such a composition, it is preferable to incorporate the pyrimidine nucleic acid-related substance into a composition containing the purine nucleic acid-related substance in a proportion of generally 0.01% by weight, preferably 1% by weight or more, and more preferably 3% by weight or more so that the proportion of the pyrimidine nucleic acid-related substance relative to the purine nucleic acid-related substance is as described above. There is no limitation to the amount of the purine nucleic acid-related substance contained in the resultant composition insofar as the amount is not below the lower limit of the above-mentioned range, but is preferably selected from the range of 0.01 to 10% by weight, more preferably 1 to 10% by weight, and still more preferably 3 to 6% by weight. The proportion of the pyrimidine nucleic acid-related substance can be suitably selected from the range of 0.0001 to 50% by weight, preferably 0.0001 to 10% by weight, and more preferably 0.0001 to 1% by weight, considering the above-described ratio of pyrimidine nucleic acid-related substance relative to purine nucleic acid-related substance.

As described above, the combined use of a pyrimidine nucleic acid-related substance with a purine nucleic acid-related substance can potentiate the cell proliferation promoting effect of the purine nucleic acid-related substance. Accordingly, the present invention also provides the use of a pyrimidine nucleic acid-related substance for potentiating the cell proliferation promoting effect of a purine nucleic acid-related substance.

(3) A Method for Promoting Cell Proliferation

The present invention also provides a method for promoting cell proliferation. The method is carried out by applying a purine nucleic acid-related substance in combination with a pyrimidine nucleic acid-related substance to the skin or mucosa.

The purine nucleic acid-related substances and the pyrimidine nucleic acid-related substances usable in the invention include the previously-described substances. A preferable example of such a purine nucleic acid-related substance is an adenine nucleic acid-related substance. Preferable among adenine nucleic acid-related substances are adenosine phosphates, metabolites thereof, and their salts, and particularly preferable are adenosine phosphates and salts thereof. Specific examples of adenosine phosphates include adenosine monophosphates, in particular adenosine 5'-monophosphate (AMP). Preferable examples of pyrimidine nucleic acid-related substances include uracil nucleic acid-related substances. Preferable among such uracil nucleic acid-related substance are uridine, uridine phosphates, and salts thereof, and particularly preferable are uridine phosphate and salts thereof. Specific examples of uridine phosphates include uridine monophosphates, in particular uridine 5'-monophosphate (UMP).

The ratio of the pyrimidine nucleic acid-related substance used in conjunction with the purine nucleic acid-related substance is 0.01 to 100 parts by weight, preferably 0.01 to 10 parts by weight, and more preferably 0.01 to 1 part by weight per part by weight of the purine nucleic acid-related substance.

In the method of the invention, there is no limitation to the manner of applying a purine nucleic acid-related substance to the skin or mucosa (hereinafter, referred to as "skin or the like") in combination with a pyrimidine nucleic acid-related substance, insofar as the purine nucleic acid-related substance and the pyrimidine nucleic acid-related substance can co-exist on the skin or mucosa. For example, a composition containing a purine nucleic acid-related substance and a pyrimidine nucleic acid-related substance may be applied to the skin or the like, or a purine nucleic acid-related substance or a composition containing the same and a pyrimidine nucleic acid-related substance or a composition containing the same may be successively applied to the skin or the like in any desired order. The above-mentioned both kinds of substances may be applied to the skin or the like by, for example, spreading or spraying.

A preferable embodiment of the method of the invention includes the manner of spreading or spraying the composition containing a purine nucleic acid-related substance and a pyrimidine nucleic acid-related substance on the skin or the like. Preferable compositions containing a purine nucleic acid-related substance and a pyrimidine nucleic acid-related substance include the compositions for cell proliferation described in (1) above.

The method of the present invention can potentiate the cell proliferation promoting effect of a purine nucleic acid-related substance to promote cell proliferation. Accordingly, the method of the present invention can be used for the purpose of anti-aging, moisturizing, anti-acne, skin whitening, anti-wrinkle, anti-sagging, anti-dullness, hair growth, anti-dandruff, nail beautifying, wound healing, etc. Preferably, the method of the invention is used for the purposes of anti-aging, moisturizing, anti-acne, skin whitening, anti-wrinkle, anti-sagging, anti-dullness, hair growth, nail beautifying, wound healing, etc. In particular, the method of the present invention is useful for the purpose of anti-wrinkle since the anti-wrinkle effect is efficiently exhibited by promoting cell proliferation.

There is no limitation to the frequencies and amount of the both kinds of substances applied to the skin or the like. For example, they may be applied in an appropriate amount to the skin or the like one to six times per day according to the age of the user (human), the gender, the intended use, the condition of the affected part of the skin, etc. More specifically, when the method of the invention is carried out by using the composition for cell proliferation described in (1) above, a single dose amount can be suitably adjusted such that the amount of the composition applied to the skin or the like is within the range of 0.5 to 10 mg/cm$^2$.

As described above, the combined use of a purine nucleic acid-related substance and a pyrimidine nucleic acid-related substance can promote cell proliferation. Accordingly, the present invention also provides a use of the purine nucleic acid-related substance and the pyrimidine nucleic acid-related substance for promoting cell proliferation. Additionally, the present invention provides the use of a purine nucleic acid-related substance and a pyrimidine nucleic acid-related substance for exhibiting an anti-wrinkle effect.

EXAMPLES

The present invention is described in further detail with reference to Examples and Formulation Examples. The scope of the invention is not limited to these Examples, however. In the following Examples and Formulation Examples, percentages are all by weight unless otherwise specified.

Example 1

In Vitro Cultured Human Keratinocyte Cell Proliferation Promoting Effect

Primary-cultured human keratinocyte (manufactured by Kurabo Industries, Ltd.) was cultured in a 10-cm petri dish, and the cultured cells were collected in the subconfluent state and then stored in a frozen state. The following experiments were conducted using those cryopreserved cells.

1. The cryopreserved cells were dissolved in HuMediaKG2 liquid culture media (manufactured by Kurabo Industries, Ltd.), the cell concentration was adjusted to 500000 cells/ml. 50 µl of thus obtained cells-containing solution was poured into each well of a test plate to adjust the cell concentration to 2500 cells/50 µl/well.

2. Adenosine monophosphate disodium solutions and uridine monophosphate disodium solutions at various concentrations were prepared using a sterilized phosphate buffer solution, and then they were filtered, followed by sterilization. To these was added a sterilized HuMediaKG2 liquid medium (manufactured by Kurabo Industries, Ltd.) to prepare culture media containing subject-solutions with various dilution factors.

3. Six hours after injecting cells into the plate wells, it was confirmed that human keratinocyte cells adhered to the wells. One of the culture media containing subject-solutions with various dilution factors (250 µl each) prepared as described above was added to each well to prepare test samples (total 300 µl each). The test samples were cultured at 37° C. under 5% $CO_2$ for two days. The test samples contained solutions at various concentrations prepared by blending uridine monophosphate disodium to adenosine monophosphate disodium solutions in which the concentration of adenosine monophosphate contained in the 300 µl of the test sample was adjusted to 0, 0.0001, 0.001, 0.01, 0.1, and 1 W/V %, so that the concentration of uridine monophosphate disodium was adjusted to 0, 0.000001 (1E-06), 0.00001 (1E-05), 0.0001, 0.001, 0.01 and 0.1 w/v % as calculated based on the concentration of the uridine monophosphate.

4. Two days after culture initiation, the proliferation of human keratinocyte cells was measured using a WST-1 reagent (manufactured by TaKaRa) based on the rise in absorbance. More specifically, 200 µl was removed from the cultured test sample (300 µl) in each well, 10 µl of the WST-1 reagent was added to each of the remaining 100 µl, followed by agitation, and the result was reacted in an incubator at 37° C. under 5% $CO_2$ for two hours. After the reaction was complete, absorbance was measured at a measurement wavelength of 450 nm and at a control wavelength of 690 nm using a multiscan ascent to evaluate from the measured absorbance the presence of cell proliferation and its extent. 10 µl of the WST-1 reagent was added to 100 µl of HuMediaKG2 liquid media (manufactured by Kurabo Industries, Ltd.) to form a blank solution.

The results are shown in FIG. 1. In FIG. 1, the abscissa represents the concentration of each uridine monophosphate disodium (UMP·2Na) sample, and the ordinate designates the number of cells at each concentration thereof with respect to the concentration of each adenosine monophosphate disodium sample (specifically, the concentration of adenosine monophosphate (AMP)) co-used with the uridine monophosphate disodium. FIG. 1 shows the relative ratio (ratio of cont.) of the number of cells (ordinate) relative to the number of cells of a comparative sample set as 1. The comparative samples ware prepared by adding no uridine monophosphate disodium to solutions containing adenosine monophosphate disodium (0, 0.0001, 0.001, 0.01, 0.1 and 1 w/v %).

FIG. 1 shows that the cell proliferation promoting effect of adenosine monophosphate disodium is potentiated and promoted by blending uridine monophosphate disodium as the pyrimidine nucleic acid-related substance into adenosine monophosphate disodium as the purine nucleic acid-related substance.

| Formulation Example 1 Lotion (pH 6.5) | |
|---|---|
| Adenosine monophosphate disodium | 3.0 (%) |
| Uridine monophosphate disodium | 0.1 |
| Polyoxyethylene hardened castor oil | 0.7 |
| Ethanol | 5.0 |
| Glycerin | 2.0 |
| Antiseptic | 0.2 |
| Aromatics | Suitable quantity |
| pH adjuster | Suitable quantity |
| Purified water | Balance |
| Total | 100.0% |

| Formulation Example 2 Milky lotions (pH 6.5) | |
|---|---|
| Adenosine monophosphate disodium | 1.5 (%) |
| Uridine monophosphate disodium | 0.01 |
| Carboxyvinyl polymer | 0.3 |
| Decaglyceryl monomyristate | 2.0 |
| Squalane | 5.0 |
| Ethanol | 1.0 |

-continued

| Formulation Example 2 Milky lotions (pH 6.5) | |
|---|---|
| Glycerin | 6.0 |
| Antiseptic | 0.2 |
| pH adjuster | Suitable quantity |
| Purified water | Balance |
| Total | 100.0% |

| Formulation Example 3 Hair restorer | |
|---|---|
| Adenosine monophosphate disodium | 10.0 (%) |
| Uridine monophosphate disodium | 1.0 |
| Salicylic acid | 0.1 |
| Ethanol | 20.0 |
| Glycerin | 2.0 |
| Antiseptic | 0.2 |
| Aromatics | Suitable quantity |
| pH adjuster | Balance |
| Total | 100.0% |

INDUSTRIAL APPLICABILITY

According to the composition for cell proliferation of the invention, since the cell proliferation promoting effect of a purine nucleic acid-related substance is potentiated by a pyrimidine nucleic acid-related substance, the composition for cell proliferation of the present invention is useful for cosmetics and external preparations for the skin (medical and quasi-medical drugs) that are effective for anti-aging, moisturizing, anti-acne, skin whitening, anti-wrinkle, anti-sagging, anti-dullness, hair growth, anti-dandruff, nail beautifying, wound healing, etc.

According to the method for potentiating the cell proliferation promoting effect of a purine nucleic acid-related substance, the cell proliferation promoting effect of the purine nucleic acid-related substance can be potentiated when used in combination with a pyrimidine nucleic acid-related substance. Thus, the method of the invention enables the preparation of a composition that exhibits excellent cell proliferation promoting effects with a small amount of the purine nucleic acid-related substance, and exhibits excellent anti-aging, moisturizing, anti-acne, skin whitening, anti-wrinkle, anti-sagging, anti-dullness, hair growth, anti-dandruff, nail beautifying, wound healing effects, etc.

Further, according to the method for promoting cell proliferation, cell proliferation can be effectively promoted, and thus the effects of anti-aging, moisturizing, anti-acne, skin whitening, anti-wrinkle, anti-sagging, anti-dullness, hair growth, anti-dandruff, nail beautifying, wound healing, etc. can be provided to the skin and mucosa.

The invention claimed is:

1. A composition for applying to the skin containing at least one purine nucleic acid-related substance chosen from adenosine monophosphate and a salt thereof, at least one pyrimidine nucleic acid-related substance chosen from uridine monophosphate and a salt thereof, and at least one additive chosen from humectants, UV absorbers, UV dispersants, plant extracts, astringents, anti-inflammatory agents, whiteners, skin function accelerators, aromatics, antiseptics, bactericides, thickeners, sequestering agents, refrigerants, and deodorizers;

wherein the composition contains 1% to 10% by weight of the purine nucleic acid-substance, and 0.0001% to 10% by weight of the pyrimidine nucleic acid-substance per total weight of the composition.

2. The composition according to claim 1, wherein the composition contains the pyrimidine nucleic acid-related substance in a ratio of 0.01 to 100 parts by weight per part by weight of the purine nucleic acid-related substance contained in the composition.

3. The composition according to claim 1, that is used for a purpose selected from the group consisting of anti-aging, moisturizing, anti-acne, skin whitening, anti-sagging, anti-dullness, anti-wrinkle, hair growth, anti-dandruff, nail beautifying, and wound healing.

4. The composition according to claim 1, that is used for a purpose selected from the group consisting of anti-aging, moisturizing, anti-acne, skin whitening, anti-sagging, anti-dullness, anti-wrinkle, hair growth, nail beautifying, and wound healing.

5. The composition according to claim 1, that is used for the purpose of an anti-wrinkle effect.

6. A composition for applying to the skin containing at least one purine nucleic acid-related substance chosen from adenosine monophosphate and a salt thereof, at least one pyrimidine nucleic acid-related substance chosen from uridine monophosphate and a salt thereof, and at least one additive chosen from humectants, UV absorbers, UV dispersants, plant extracts, astringents, anti-inflammatory agents, whiteners, skin function accelerators, aromatics, antiseptics, bactericides, thickeners, sequestering agents, refrigerants, and deodorizers;

wherein the composition contains 1% to 10% by weight of the purine nucleic acid-substance per total weight of the composition, and 0.01 to 1 part by weight of the pyrimidine nucleic acid-substance per part by weight of the purine nucleic acid-substance.

* * * * *